United States Patent
Blackwell et al.

(10) Patent No.: US 8,852,089 B2
(45) Date of Patent: Oct. 7, 2014

(54) INSTRUMENTATION FOR TISSUE RETRACTION

(75) Inventors: Jonathan Blackwell, Cordova, TN (US); Michael MacMillan, Gainesville, FL (US); Richard Thomas Hackett, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1362 days.

(21) Appl. No.: 11/888,566

(22) Filed: Aug. 1, 2007

(65) Prior Publication Data
US 2009/0036746 A1    Feb. 5, 2009

(51) Int. Cl.
A61B 1/32    (2006.01)
A61B 1/018    (2006.01)

(52) U.S. Cl.
USPC ........... 600/210; 600/214; 600/219; 600/222; 600/225

(58) Field of Classification Search
USPC ....... 217/96; 600/201–246; 604/264; 606/57, 606/90, 105, 282, 191–200, 190, 129–130, 606/96–98
See application file for complete search history.

(56) References Cited

U.S. PATENT DOCUMENTS

| | | | | |
|---|---|---|---|---|
| 5,027,793 A | * | 7/1991 | Engelhardt et al. | 600/210 |
| 5,913,818 A | * | 6/1999 | Co et al. | 600/204 |
| 5,928,139 A | * | 7/1999 | Koros et al. | 600/205 |
| 5,944,658 A | * | 8/1999 | Koros et al. | 600/232 |
| 6,007,487 A | * | 12/1999 | Foley et al. | 600/235 |
| 6,083,154 A | * | 7/2000 | Liu et al. | 600/234 |
| 6,929,606 B2 | * | 8/2005 | Ritland | 600/201 |
| 6,945,933 B2 | * | 9/2005 | Branch et al. | 600/210 |
| 7,909,848 B2 | * | 3/2011 | Patel et al. | 606/201 |
| 2004/0002629 A1 | * | 1/2004 | Branch et al. | 600/210 |
| 2004/0176665 A1 | | 9/2004 | Branch et al. | |
| 2004/0230191 A1 | | 11/2004 | Frey et al. | |
| 2005/0234304 A1 | * | 10/2005 | Dewey et al. | 600/210 |
| 2005/0277812 A1 | * | 12/2005 | Myles | 600/231 |
| 2008/0045956 A1 | * | 2/2008 | Songer et al. | 606/61 |
| 2008/0221394 A1 | * | 9/2008 | Melkent et al. | 600/201 |
| 2008/0221574 A1 | * | 9/2008 | Cavallazzi et al. | 606/62 |

* cited by examiner

*Primary Examiner* — Matthew Lawson
*Assistant Examiner* — Zade Coley
(74) *Attorney, Agent, or Firm* — Sorell, Lenna & Schmidt, LLP (57) ABSTRACT

Instrumentation for retracting tissue comprising a retractor member including a sidewall defining an axial passage extending along a length thereof and a lateral opening in transverse communication with the passage. A pin member is disposed within the passage and includes a distal end portion positionable adjacent the distal end of the retractor member, with at least a portion of the pin member positioned adjacent and visible through the lateral opening. In another embodiment, the retractor member includes a sidewall having a main sidewall portion defining a first wall thickness, and an enlarged sidewall portion extending axially along a length of the sidewall and defining a second wall thickness greater than the first wall thickness, with the sidewall defining an axial passage extending through the enlarged sidewall portion. A pin member is disposed within the passage and includes a distal end portion positionable adjacent the distal end of the retractor member.

38 Claims, 6 Drawing Sheets

INSTRUMENTATION FOR TISSUE RETRACTION

FIELD OF THE INVENTION

The present invention generally relates to surgical instrumentation, and more particularly relates to instrumentation for retracting tissue.

BACKGROUND

Traditional surgical procedures for pathologies located within the body can cause significant trauma to the intervening tissues. These procedures often require a long incision, extensive muscle stripping, prolonged retraction of tissues, denervation and/or devascularization of tissue. These procedures can also require lengthy operating room times and several weeks of post-operative recovery time due to damage and/or destruction of tissue resulting from the surgical procedure. In some cases, these invasive procedures may lead to permanent scarring and prolonged pain that can be more severe than the pain leading to the surgical intervention.

The development of percutaneous procedures has yielded significant improvements in reducing recovery time and post-operative pain because of minimization of the dissection of tissue. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development of instrumentation for retracting tissue in a minimally invasive manner.

SUMMARY

The present invention generally relates to surgical instrumentation, and more particularly relates to instrumentation for retracting tissue in a minimally invasive manner. While the actual nature of the invention covered herein can only be determined with reference to the claims appended hereto, certain forms of the invention that are characteristic of the preferred embodiments disclosed herein are described briefly as follows.

In one form of the present invention, instrumentation is provided for retracting tissue, comprising a retractor member including a sidewall extending along a longitudinal axis and having a length extending between a distal end and a proximal end, with the sidewall defining an axial passage extending generally along the length from the distal end toward the proximal end, and with the sidewall defining a lateral opening in transverse communication with the axial passage. The instrumentation further comprises a pin member disposed within the axial passage of the retractor member and including a distal end portion positionable adjacent the distal end of the retractor member with at least a portion of the pin member positioned adjacent and visible through the lateral opening.

In another form of the present invention, instrumentation is provided for retracting tissue, comprising a retractor assembly including at least two retractor members that cooperate to define a working space therebetween extending generally along a longitudinal axis, with each of the at least two retractor members including a sidewall having a length extending between a distal end and a proximal end, and with at least one of the sidewalls defining an axial passage extending generally along the length from said distal end toward said proximal end and defining a lateral opening in transverse communication with the axial passage. The instrumentation further comprises a pin member disposed within the axial passage and including a distal end portion positionable adjacent the distal end of the retractor member with at least a portion of the pin member positioned adjacent and visible through the lateral opening.

In a further form of the present invention, instrumentation is provided for retracting tissue, comprising a retractor member including a sidewall extending along a longitudinal axis and having a length extending between a distal end and a proximal end, with the sidewall including a main sidewall portion defining a first wall thickness and an enlarged sidewall portion extending axially along the length and defining a second wall thickness greater than the first wall thickness, and with the sidewall defining an axial passage extending through the enlarged sidewall portion from the distal end toward the proximal end. The instrumentation further comprises a pin member disposed within the axial passage and including a distal end portion positionable adjacent the distal end of the retractor member.

In yet another form of the present invention, instrumentation is provided for retracting tissue, comprising a retractor member including a sidewall extending along a longitudinal axis and having a length extending between a distal end and a proximal end, with the sidewall including a laterally-facing surface and a sidewall protrusion projecting transversely from the laterally-facing surface and extending axially along the length, and with the retractor member defining an axial passage extending through the sidewall protrusion from the distal end toward the proximal end. The instrumentation further comprises a pin member disposed within the axial passage and including a distal end portion positionable adjacent the distal end of the retractor member.

In still another form of the present invention, instrumentation is provided for retracting tissue, comprising a retractor member including a sidewall extending along a longitudinal axis and having a length extending between a distal end and a proximal end, and an anchor member extending from the distal end of the sidewall and configured for engagement with bone tissue to anchor the retractor member to bone.

It is one object of the present invention to provide improved instrumentation for retracting tissue. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

The present invention provides instrumentation for performing, for example, percutaneous surgery, including spinal surgeries that include one or more techniques such as laminotomy, laminectomy, foramenotomy, facetectomy, discectomy, interbody fusion, spinal nucleus or disc replacement, and implant insertion including plates, rods and bone engaging fasteners. The surgical procedure is performed via a working channel or space extending through the skin and tissue of the patient which is provided by retractor instrumentation. Viewing of the surgical site at the working end of the retractor instrumentation can be accomplished with viewing instruments mounted on the retractor instrumentation, positioned over the retractor instrumentation, positioned within other portals in the body, and/or through a viewing system such as lateral fluoroscopy. The retractor instrumentation is movable in situ to increase the size of the working channel to facilitate access to the working space at the distal end of the retractor instrumentation while minimizing trauma to the adjacent tissue and other anatomic structures. The retractor instrumentation can be used in association with any surgical approach to the spine, including anterior, posterior, posterior mid-line, lateral, postero-lateral, and/or antero-lateral approaches. The retractor instrumentation can also be used in regions of the body other than the spinal region.

Figure 1:
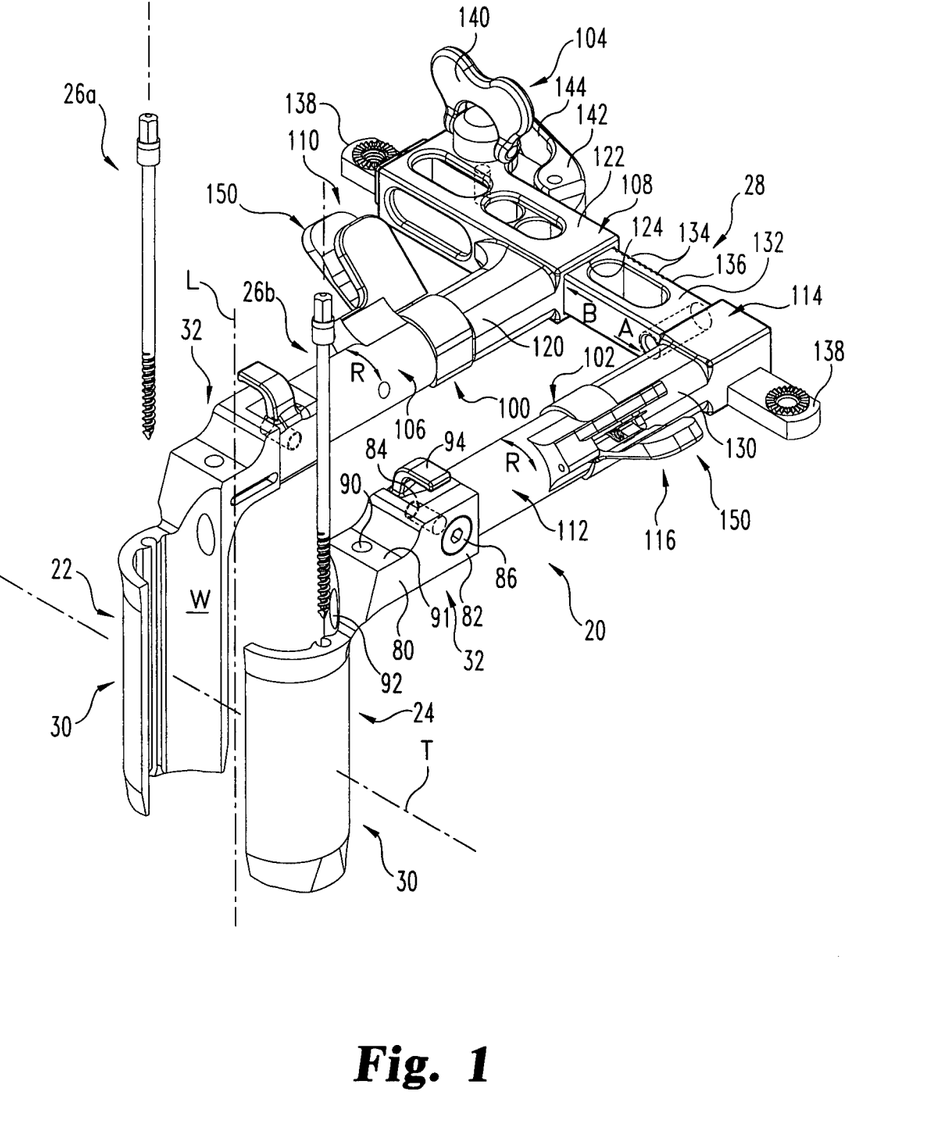
FIG. 1 is a perspective view of a retractor instrument according to one embodiment of the present invention.

Referring to FIG. 1 shown therein is an instrument 20 for retracting tissue according to one form of the present invention. In the illustrated embodiment, the retractor instrument 20 includes a pair of retractor members 22, 24 extending generally along a longitudinal axis L, a pair of pin members 26a, 26b associated with the retractor members 22, 24, and an actuator device 28 coupled to the retractor members 22, 24. As will be discussed in greater detail below, the retractor members 22, 24 each have an arcuate or semi-circular transverse cross section and cooperate to define a generally tubular configuration that provides a working channel or space W to a surgical site. However, other shapes and configurations of the retractor members 22, 24 are also contemplated as falling within the scope of the present invention. The pin members 26a, 26b are configured to couple the retractor members 22, 24 to one or more anatomic structures adjacent the surgical site, such as, for example, to one or more vertebral bodies.

The actuator device 28 is configured to displace the retractor members 22, 24 apart generally along a transverse axis T to retract tissue and to increase the size of the working channel W to the surgical site. The components of the retractor instrument 20 may be formed of stainless steel, titanium, or any other suitable material. Further details regarding the elements and features associated with the retractor instrument 20 will be set forth below.

Figure 2:
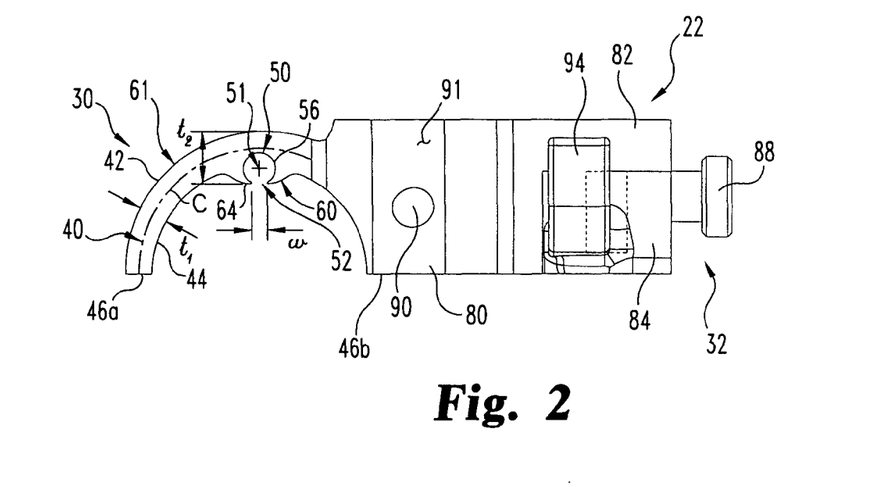
FIG. 2 is a top view of the left-side retractor blade illustrated in FIG. 1.
Figure 3:
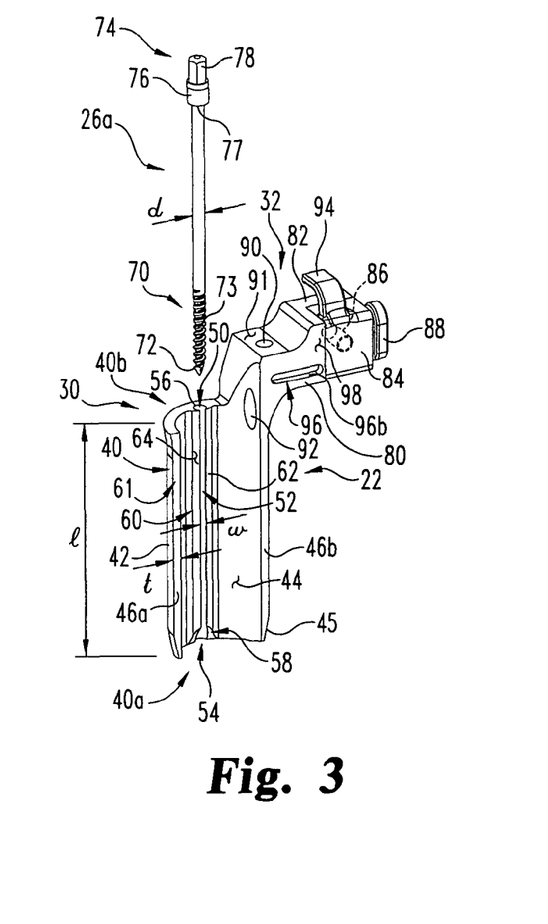
FIG. 3 is a perspective view of the retractor blade and pin member illustrated in FIG. 1, as shown in a non-assembled state.
Figure 4:
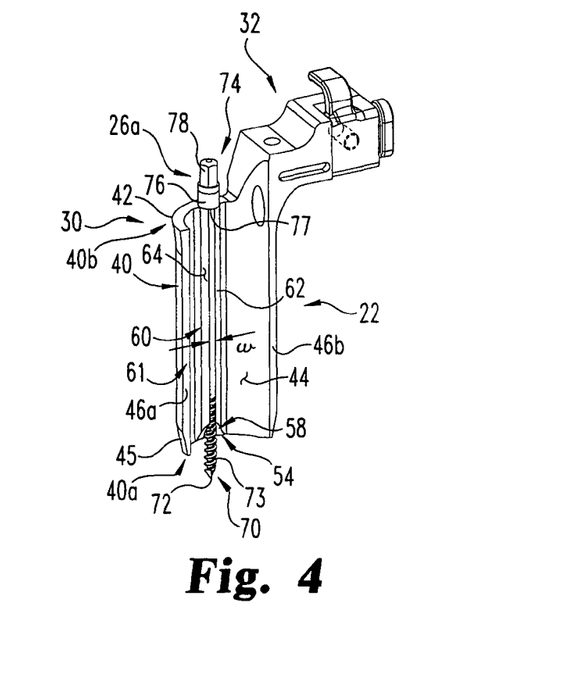
FIG. 4 is a perspective view of the retractor blade and pin member illustrated in FIG. 1, as shown in an assembled state.

Referring collectively to FIGS. 2-4, shown therein are further details regarding the retractor member 22 and the pin member 26a. It should be understood that, except where indicated below, the retractor members 22, 24 are configured as mirror images of one another relative to a plane intersecting the longitudinal axis L, and the pin members 26a, 26b are configured identical to one another.

In one embodiment, the retractor members 22, 24 are configured to retract tissue, such as, for example, skin, muscle, bone, neural structures including nerves, vascular structures and/or other anatomic structures, to provide a working channel or space W to the surgical site. In the illustrated embodiment, the retractor instrument 20 includes two retractor members 22, 24 positioned generally opposite one another relative to the longitudinal axis L. However, it should be understood that in other embodiments, the retractor instrument 20 may be provided with three, four, or five or more retractor members positioned peripherally about the longitudinal axis L. It should also be understood that the retractor instrument 20 may be provided with a single retractor member. In one embodiment, the retractor instrument 20 may be provided with a single tubular retractor member defining an inner working channel or space W extending along the longitudinal axis L. In another embodiment, the retractor instrument 20 may be provided with a single retractor member having an open, blade-like configuration.

In the illustrated embodiment, each of the retractor members 22, 24 includes a blade portion 30 for retracting tissue and a coupler portion 32 for mounting the blade portion 30 to the actuator device 28 (FIG. 1). The retractor blade 30 includes a sidewall 40 extending generally along the longitudinal axis L and has a length l extending between a distal end 40a and a proximal end 40b. The sidewall 40 has an outer or exterior surface 42 and an inner or interior surface 44. The distal end 40a of the sidewall 40 may be provided with a taper or bevel 45 to facilitate insertion through skin and tissue, although a non-beveled distal end is also contemplated. In the illustrated embodiment, the sidewall 40 of the retractor blade 30 has an arcuate configuration, and more specifically a semi-tubular or semi-cylindrical configuration. However, it should be understood that other shapes and configurations of the sidewall 40 are also contemplated as falling within the scope of the present invention. Additionally, the sidewall 40 includes a pair of longitudinal edges 46a, 46b extending along the length l between the distal and proximal ends 40a, 40b. The longitudinal edges 46a, 46b of the sidewalls 40 defined by adjacent retractor blades 30 are positioned adjacent one another to provide a retractor assembly having a tubular configuration that substantially surrounds and encloses the working channel or space W extending generally along the longitudinal axis L and entirely along the length I between the distal and proximal ends 40a, 40b of the retractor sidewalls 40.

The sidewall 40 of the retractor blade 30 defines an axial passage 50 through a sidewall thickness t and extending generally along the longitudinal axis L. The axial passage 50 extends along at least a portion of the sidewall length l from the distal end 40a toward the proximal end 40b. The sidewall 40 further defines a lateral opening 52 extending through a lateral surface of the sidewall 40 in transverse communication with the axial passage 50. The axial passage 50 is sized and configured to receive one of the pin members 26a, 26b therein, and the lateral opening 52 is sized and configured such that at least a portion of the pin member 26a, 26b is visible therethrough. Further details regarding the pin members 26a, 26b will be set forth below.

In one embodiment of the invention, the axial passage 50 extends axially from the distal end 40a of the sidewall 40 toward the proximal end 40b so as to define an opening 54 at the distal end 40a from which a distal end portion of the pin member 26a, 26b extends. In the illustrated embodiment, the axial passage 50 extends entirely along the length l of the sidewall 40 from the distal end 40a to the proximal end 40b so as to define openings 54, 56 at each end of the sidewall 40 through which portions of the pin member 26a, 26b may extend. In the illustrated embodiment, each of the retractor blades 30 includes a single axial passage 50. However, in other embodiments, either or both of the retractor blades 30 may includes two or more axial passages 50 for receipt of a corresponding number of pin members 26a, 26b. In another embodiment, only one of the retractor blades 30 is provided with an axial passage 50. Additionally, although the axial passage 50 is illustrated as having a circular configuration, it should be understood that other shapes and configurations are also contemplated, including, for example, an oblong or elliptical shape, a square or rectangular shape, a polygonal shape or any other suitable shape or configuration.

Although the axial passage 50 is illustrated as extending generally parallel with the longitudinal axis L, it should be understood that the axial passage 50 may extend transverse to the longitudinal axis L at an oblique angle and/or may be laterally skewed relative to the longitudinal axis L. Furthermore, in one embodiment, the center 51 of the axial passage 50 is laterally offset from the centerline C of the sidewall thickness t. In the illustrated embodiment, the center 51 of the axial passage 50 is laterally offset from the centerline C toward the interior surface 44 of the sidewall 40. However, in other embodiments, the center 51 of the axial passage 50 may be laterally offset from the centerline C toward the exterior surface 42 of the sidewall 40, or may be positioned along the centerline C. Additionally, in the illustrated embodiment, the axial passage 50 is approximately centered along the width of the sidewall 40 relative to the central longitudinal axis L (i.e., approximately centered between the longitudinal edges 46a, 46b). However, in other embodiments, the axial passage 50 may be offset along the width of the sidewall 40 toward either of the longitudinal edges 46a, 46b.

In one embodiment, the lateral opening 52 is axially positioned adjacent the distal end 40a of the sidewall 40 of the retractor blade 30. In a further embodiment, the lateral opening 52 extends axially from the distal end 40a of the sidewall 40 toward the proximal end 40b such that at least the distal end of the pin member 26a, 26b is visible through the lateral opening or window 52 at the distal end 40a of the sidewall 40, the purpose of which will be discussed below. In the illustrated embodiment, the lateral opening or window 52 extends entirely along the length l of the sidewall 40 from the distal end 40a to the proximal end 40b. However, it should be understood that the lateral opening may extend along other portions of the sidewall 40 and along various lengths of the sidewall 40. In the illustrated embodiment, the lateral opening 52 extends through interior surface 44 of the sidewall 40 and is positioned in communication with the working channel or space W. However, in other embodiments, the lateral opening 52 may extend through the exterior surface 42 of the sidewall 40 opposite the working channel or space W. In further embodiments, the lateral opening 52 may extend through each of the exterior and interior surfaces 44 adjacent the distal end 40a of the sidewall 40 to provide visualization of the distal end portion of the pin member 26a, 26b from opposite directions. In still other embodiments, the lateral opening 52 may extend through other portions of the sidewall 40, including the longitudinal edges 46a, 46b. It should further be understood that in other embodiments, the sidewall 40 need not necessarily be provided with a lateral opening 52.

In the illustrated embodiment, the lateral opening 52 is generally aligned with the axial passage 50 and has a generally rectangular configuration defining a width w that is less than an outer dimension or diameter d of the pin member 26a, 26b so as to retain the pin member 26a, 26b within the axial passage 50, yet large enough to provide a relatively unobstructed lateral view of at least a portion of the pin member 26a, 26b within the axial passage 50. In one embodiment, the width w of the lateral opening 52 is approximately one-third of the outer diameter d of the pin member 26a, 26b. However, in other embodiments of the invention, the width w may take on other sizes relative to the outer diameter d of the pin member 26a, 26b. It should also be understood that the width w of the lateral opening 52 does not necessarily have to be uniform, but can instead vary along the length l of the sidewall 40. For example, in other embodiments, the width w of the lateral opening 52 may be sized larger adjacent the distal end 40a of the sidewall 40 relative to other portions of the lateral opening 52 so as to define an enlarged lateral opening 58 to provide greater visibility of the pin member 26a, 26b adjacent the distal end 40a of the sidewall 40. In one specific embodiment, the width w of the lateral opening 52 adjacent the distal end 40a of the sidewall 40 may be substantially equal to the inner dimension or diameter of the axial passage 50 so as to provide greater visualization of the pin member 26a, 26b adjacent the distal end 40a. In another embodiment, the width w of the lateral opening may vary along the length l of the sidewall 40. It should further be understood that the lateral opening 52 does not necessarily have to extend continuously along the length l of the sidewall 40. For example, in other embodiments, the lateral opening 52 may be interrupted so as to define a plurality of individual openings or windows 52 extending axially along the sidewall length l.

In the illustrated embodiment of the invention, the sidewall 40 of the retractor blade 30 includes an enlarged sidewall portion or axial region 60 extending generally along the longitudinal axis L, with the axial passage 50 extending through the enlarged sidewall portion 60. As will be discussed in greater detail below, the enlarged sidewall portion 60 has a wall thickness sized to accommodate the axial passage 50, with the remaining sidewall thickness being minimized to correspondingly reduce the cross-sectional footprint of the retractor blade 30. More specifically, the sidewall 40 includes a main sidewall portion 61 defining a first wall thickness $t_1$, and an enlarged sidewall portion 60 extending axially along the sidewall length l and defining a second wall thickness $t_2$ that is greater than the first wall thickness $t_1$. In one specific embodiment, the second wall thickness $t_2$ is about fifty percent greater than the first wall thickness $t_1$. However, it should be understood that the enlarged sidewall portion 60 can be provided with other wall thickness $t_2$ relative to the wall thickness $t_1$ of the main sidewall portion 61.

In one embodiment of the invention, the enlarged sidewall portion 60 extends axially from the distal end 40a of the sidewall 40 toward the proximal end 40b, with the axial passage 50 extending substantially entirely along the enlarged sidewall portion 60. In the illustrated embodiment, the enlarged sidewall portion 60 extends entirely along the length l of the sidewall 40 from the distal end 40a to the proximal end 40b. However, it should be understood that the enlarged sidewall portion 60 may extend along any portion of the sidewall 40 and along less than the entire sidewall length l. For example, the enlarged sidewall portion 60 may terminate short of the distal end 40a of the sidewall 40. Elimination of the enlarged sidewall portion 60 adjacent the distal end 40a of the sidewall 40 would in turn provide the lateral opening 50 with a greater width w adjacent the distal end 40a. It should further be understood that in other embodiments, the sidewall 40 need not necessarily be provided with an enlarged sidewall portion 60, but may instead define a substantially uniform sidewall thickness t.

The enlarged sidewall portion 60 defines a lateral protrusion 62 extending transversely from a laterally-facing surface of the sidewall 40, with the lateral protrusion 62 defining the lateral opening 52. In the illustrated embodiment, the lateral protrusion 62 extends transversely from the interior surface 44 of the sidewall 40 and projects inwardly into the working channel or space W. However, in other embodiments, the lateral protrusion 62 may extend transversely from the exterior surface 42 of the sidewall 40, projecting outwardly away from the working channel or space W. In still other embodiments, the lateral protrusion 62 may extend transversely from both the interior surface 44 and the exterior surface 42 of the sidewall 40 so as to define a pair of lateral protrusions extending in generally opposite directions. In the illustrated embodiment of the invention, the enlarged sidewall portion 60 is generally aligned with the axial passage 50 and has a width and wall thickness $t_2$ sized to accommodate the axial passage 50. The lateral protrusion 62 defined by the enlarged sidewall portion 60 includes a laterally-facing surface 64 having a rounded or arcuate configuration. However, other shapes and configurations of the lateral protrusion 62 are also contemplated, including, for example, planar or polygonal shapes and configurations. It should also be understood that the width and wall thickness $t_2$ of the enlarged sidewall portion 60 do not necessarily have to be uniform, but can instead vary along the length l of the sidewall 40. It should further be understood that the enlarged sidewall portion 60 does not necessarily have to extend continuously along the length l of the sidewall 40, but may instead be axially interrupted along the length l to provide a plurality of enlarged sidewall portions 60 axially offset from one another and positioned in general alignment along the longitudinal axis L.

As indicated above, the pin members 26a, 26b are configured to couple the retractor members 22, 24 to one or more anatomic structures adjacent the surgical site, such as, for example, to one or more vertebral bodies. The pin members 26a, 26b are positioned within the axial passages 50 of the retractor blades 30 and are sized such that a distal portion 70 may be positioned to extend through the distal opening 54 of the passage 50 and into engagement with bone tissue. In the illustrated embodiment, the distal portion 70 of the pin members 26a, 26b defines a pointed or tapered distal end 72 to facilitate penetration into bone tissue, and also defines external threads 73 configured for threading engagement with the bone tissue. However, it should be understood that other pin configurations are also contemplated, including non-threaded pin configurations having a smooth outer surface, and/or pin configurations having a rounded or blunt distal end. The pin members 26a, 26b may be provided with an overall pin length that is greater than the length l of the sidewall 40 such that when the distal portion 70 is positioned to extend through the distal opening 54, a proximal portion 74 of the pin members 26a, 26b extends through the proximal opening 56 of the passage 50 for engagement by a driving tool (not shown).

The proximal portion 74 of the pin members 26a, 26b includes an enlarged region 76 defining a shoulder 77 which engages the proximal end 40b of the sidewall 40 as the pin member 26a, 26 is driven into bone tissue to compress the distal end 40a of the sidewall 40 into abutting engagement with the bone tissue. The proximal portion 74 of the pin members 26a, 26b may also be provided with a feature which facilitates engagement by a driving tool (not shown). In the illustrated embodiment, the proximal portion 74 includes a hexagonal-shaped projection 78 sized and configured for engagement by a driving tool having a correspondingly shaped socket. However, the proximal portion 74 of the pin member may be provided with other features suitable to facilitate driving the pin member into bone tissue including, for example, a hexagonal-shaped socket, a slot, or any other suitable driving feature. Additionally, although the pin members 26a, 26b are illustrated as having a circular outer cross section which corresponds to the circular inner cross section of the axial passage 50, it should be understood that other shapes and configurations are also contemplated, including, for example, an oblong or elliptical shape, a square or rectangular shape, a polygonal shape or any other suitable shape or configuration.

As indicated above, each of the retractor members 22, 24 includes a blade portion 30 for retracting tissue and a coupler portion 32 for mounting the blade portion 30 to the actuator device 28. The coupler portion 32 extends transversely from a proximal region of the blade portion 30 so as to facilitate engagement of the retractor members 22, 24 to the actuator device 28 without obstructing the working channel W between the retractor blades 30. The coupler portion 32 includes a mounting block 80, a mounting flange 82 and a coupler 84 removably attached to the mounting flange 82 via a fastener 86. The coupler 84 includes a mounting foot 88 configured for engagement with the actuator 28. The mounting block 80 includes a passage 90 extending from an upper mounting block surface 91 and opening onto the interior surface 44 of the retractor blade 30 so as to define an opening 92 in communication with the working channel W. A portion of a surgical instrument (not shown), such as a light source or viewing source, may be positioned through the passage 90, out the opening 92 and into working channel W. Positioning of the surgical instrument through the passage 90 avoids obstruction of the proximal end opening of the working channel W. A retaining member 94 extending from the coupler 84 may be used to secure one or more surgical instruments in position relative to the retractor blade 30. The mounting block 80 also includes an alignment feature 96 arranged along a laterally-facing surface 98 (FIG. 3). The alignment features 96 of the opposing retractor members 22, 24 cooperate with one another to facilitate and maintain alignment between the retractor blades 30 when the longitudinal edges 46a, 46b of the retractor blades are positioned in close proximity to one another. In the illustrated embodiment, the alignment features comprise a tongue or projection 96a associated with one of the retractor members (FIG. 8) that is positioned within a groove or recess 96b associated with the other retractor member (FIG. 3). However, is should be understood that other types and configurations of alignments features are also contemplated as would occur to one of skill in the art.

Referring to FIG. 1, as indicated above, the actuator device 28 is configured to displace the retractor members 22, 24 apart generally along the transverse axis T to retract tissue and to increase the size of the working channel or space W. In one embodiment, the first and second retractor members 22, 24 are releasably engaged to the actuator device 28 via the couplers 84 and the mounting feet 88. However, in other embodiments, the first and second retractor members 22, 24 may be non-releasably engaged to the actuator device 28. In the illustrated embodiment of the invention, the actuator device 28 is configured to displace the retractor members 22, 24 relative to one another to retract tissue and to vary the size of the working channel W, and is also configured to allow the retractor members 22, 24 to pivot relative to one another to retract tissue and to vary the size and shape of the working channel W.

In the illustrated embodiment, the actuator device 28 includes first and second connection assemblies 100, 102 that are coupled to respective ones of the retractor members 22, 24, and a drive mechanism 104 configured to selectively displace the connection assemblies 100, 102 relative to one another to correspondingly displace the retractor members 22, 24 toward and away from one another generally along the transverse axis T. The first connection assembly 100 includes a support member 106 coupled to the coupler portion 32 of the retractor member 22, and a drive member 108 pivotally coupled to the support 106 via a pivot mechanism 110. Similarly, the second connection assembly 102 includes a support member 112 coupled to the coupler portion 32 of the retractor member 24, and a drive member 114 pivotally coupled to the support member 112 via a pivot mechanism 116.

The support members 106, 112 are arranged generally parallel to one another and each include a distal coupling portion (not shown) configured for engagement with the coupler portion 32 of the retractor members 22, 24. In one embodiment, the distal coupling portion of the support member 106, 112 defines a recess or receptacle (not shown) sized and configured for receiving the mounting foot 88 of the coupler portion 32 therein to engage the support members 106, 112 with the retractor members 22, 24. The drive member 108 of the first connection assembly 100 includes a rod portion 120 coupled to the support member 106 via the pivot mechanism 110, and a gear housing 122 extending transversely from the rod portion 120 and defining an inner passage 124. The drive member 114 of the second connection assembly 102 includes a rod portion 130 coupled to the support member 112 via the pivot mechanism 116, and a rack arm 132 extending transversely from the rod portion 130 and sized for slidable displacement within the inner passage 124 of the gear housing 122. The rack arm 132 defines a number of gear or ratchet teeth 134 extending along an exterior surface 136. Each of the drive members 108, 114 may be provided with a mounting tab 138 configured to mount various devices or instruments to the retractor instrument 20.

The drive mechanism 104 is rotatably mounted to the gear housing 122 of the drive member 108 and includes a drive gear or pinion (not shown) having teeth that mesh with the teeth 134 formed along the rack arm 132. The drive mechanism 104 further includes a handle 140 which facilitates manual rotation of the drive gear. Rotation of the drive gear displaces the rack arm 132 along the inner passage 124 of the gear housing 122, which in turn displaces the connection assemblies 100, 102 relative to one another to correspondingly displace the retractor members 22, 24 toward and away from one another generally along the transverse axis T. A locking mechanism 142 is mounted to the gear housing 122 and includes a pawl (not shown) which engages the teeth 134 formed along the rack arm 132 to inhibit movement of the gear housing 122 in a first direction (i.e., in the direction of arrow A) while allowing movement in an opposite second direction (i.e., in the direction of arrow B). The locking mechanism 142 is thereby configured to allow the retractor members 22, 24 to be displaced apart along the transverse axis T, while inhibiting displacement of the retractor members 22, 24 toward one another. The locking mechanism 142 may be spring-biased to bias the pawl into engagement with the teeth 134, and may include a release handle 144 to facilitate manual disengagement of the pawl from the teeth 134 to allow movement of the gear housing 122 in the direction of arrow A.

The pivot mechanisms 110, 116 associated with the connection assemblies 100, 102 are configured to allow selective rotational movement of the support members 106, 112 relative to the drive members 108, 114 in the direction of arrows R, which in turn allows selective pivotal movement of the retractor members 22, 24, including the retractor blades 30, toward and away from one another generally along the transverse axis T. The pivot mechanisms 110, 116 each include a lever assembly 150 and a locking device (not shown) which are operable to allow selective rotation of the support members 106, 112 relative to the drive members 108, 114.

Although a specific configuration of the actuator device 28 has been illustrated and described herein, it should be understood that various types of actuator devices are contemplated for use in association with the present invention. Further details regarding the actuator device 28 and/or alternative configurations of actuator devices or separation instruments are illustrated and described in U.S. Patent Application Publication No. 2005/0234304, the contents of which are expressly incorporated herein by reference. Additionally, it should be understood that an actuator device or separation instrument need not necessarily be used in association with the present invention. Instead, the retractor members 22, 24 may be manually manipulated by the surgeon, or can be mounted in a stationary position via a mounting frame or other types of mounting structures.

Figures 5, 6, 7:
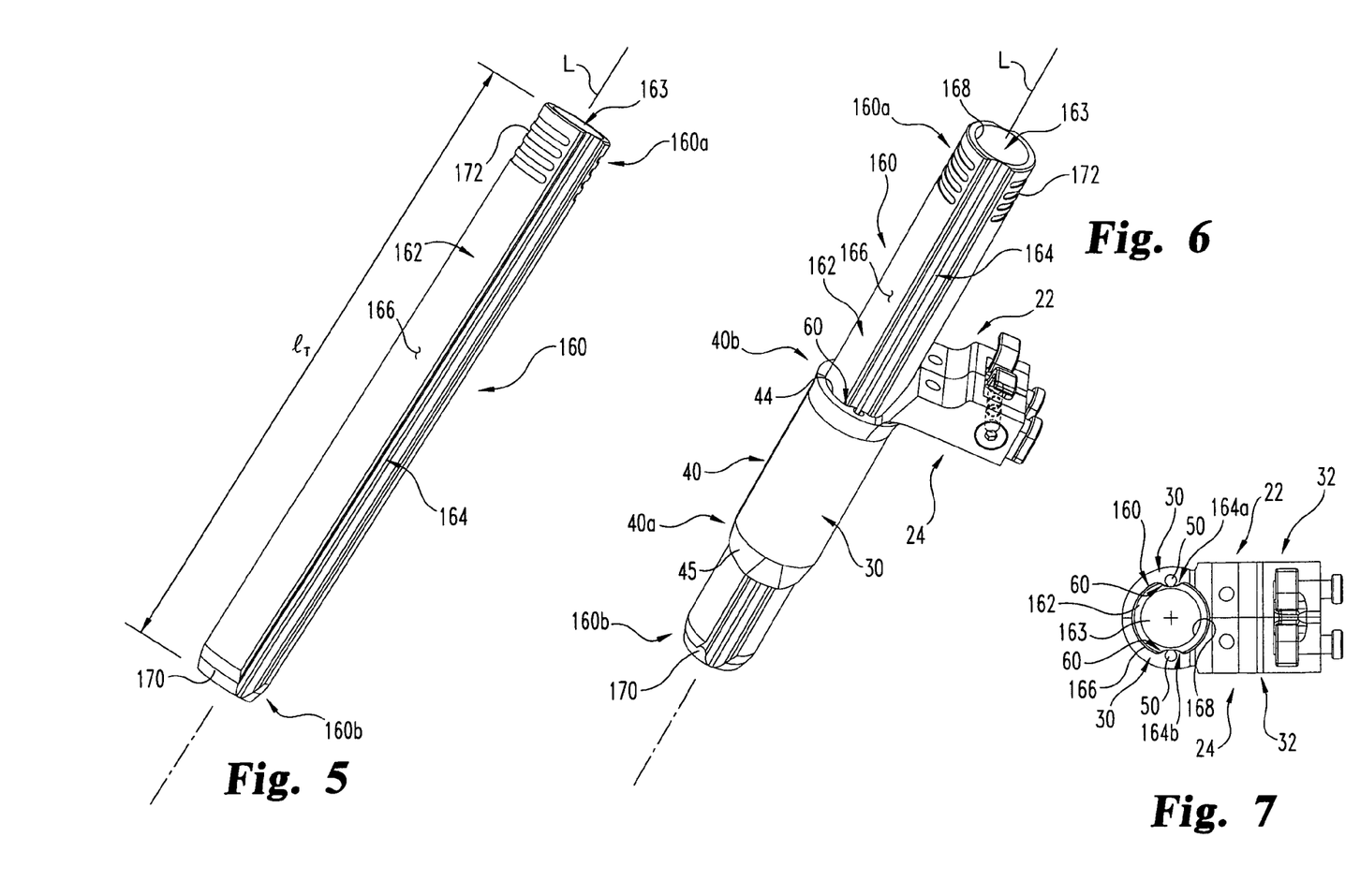
FIG. 5 is a perspective view of a dilator tube according to one embodiment of the present invention.
FIG. 6 is a perspective view of the dilator tube illustrated in FIG. 4, as assembled with the retractor blades illustrated in FIG. 1.
FIG. 7 is a top view of the assembly illustrated in FIG. 6.

Referring to FIGS. 5-7, shown therein is a tissue dilator 160 for use in association with the retractor instrument 20. The tissue dilator 160 is used to retract tissue prior to insertion of the retractor members 22, 24 into the patient. In the illustrated embodiment, the tissue dilator 160 has a tubular configuration including a tube wall 162 having a tube length $l_T$ extending generally along the longitudinal axis L between proximal and distal ends 160a, 160b and defining a hollow interior 163. However, it should be understood that the tissue dilator 160 can take on other configurations, including a generally solid, rod-like configuration. The tube wall 162 includes at least one groove or recess 164 extending axially along the tube length $l_T$ and sized to slidably receive the enlarged sidewall portion 60 of the retractor blade 30 therein. In the illustrated embodiment, the tube wall 162 includes a pair of axially-extending grooves or recesses 164a, 164b positioned diametrically opposite one another for receipt of the enlarged sidewall portions 60 defined by the adjacent retractor blades 30 of the retractor member 22, 24. However, it should be understood that the dilator tube 160 may include a single axially extending groove or recess, or three or more axially extending grooves or recesses.

In the illustrated embodiment, the axially-extending grooves or recesses 164a, 164b extend along the entire tube length $l_T$ from the proximal end 160a to the distal end 160b. However, it is also contemplated that the grooves or recesses 164a, 164b may extend along less than the entire length $l_T$ of the tube wall 162. Additionally, although the grooves or recesses 164a, 164b are illustrated as extending along an exterior surface 166 of the dilator tube 160, it should be understood that the grooves or recesses 164a, 164b may extend along an interior surface 168 of the dilator tube 160. In the illustrated embodiment, the grooves or recesses 164a, 164b each have a generally U-shape or rounded/arcuate inner profile that corresponds to the outer profile of the enlarged sidewall portions 60 of the retractor blades 30. However, other shapes and configurations of the grooves or recesses 164a, 164b are also contemplated, including, for example, planar or polygonal shapes and configurations.

The distal end 160a of the dilator tube 160 may be provided with a tapered exterior surface 170 to facilitate introduction of the dilator tube 160 through an incision in the skin and into an opening in tissue and/or to retract tissue. Additionally, the proximal end 160b of the dilator tube 160 may be provided with a number of grooves or recesses 172 to facilitate mechanical grasping of the dilator tube 160 by a gripping instrument or manual grasping by the surgeon. Once the distal end portion of the dilator tube 160 is positioned within the tissue opening, the retractor members 22, 24 may be inserted over and axially displaced along the dilator tube 160 until the distal ends 40a of the retractor blade sidewalls 40 are inserted into the tissue opening to provide additional dilation or retraction of the tissue. In one embodiment, during initial insertion of the retractor instrument 20, the retractor members 22, 24 are initially positioned adjacent one another with the longitudinal edges 46a, 46b of the retractor blade sidewalls 40 positioned in close proximity to one another such that the retractor blades 30 define a tubular configuration having an inner dimension or diameter that is slightly greater than the outer diameter of the dilator tube 160. In this manner, the retractor members 22, 24 can be axially displaceable over the dilator tube 160, with the enlarged sidewall portions 60 of the retractor blades 30 slidably displaced along the axially-extending grooves or recesses 164a, 164b formed along the exterior surface 166. As should be appreciated, if the dilator tube 160 was not provided with the axially-extending grooves or recesses 164a, 164b for receipt of the enlarged sidewall portions 60 of the retractor blades 30, the difference between the outer diameter of the dilator tube 160 and the inner diameter of the working channel W defined by the retractor members 22, 24 would be increased, which would correspondingly increase the difference between the outer diameter of the dilator tube 160 and the outer diameter of the retractor members 22, 24. As a result, the amount of tissue retraction or separation caused by insertion of the distal ends of the retractor blades into the tissue opening would be significantly increased, which could potentially result in damage or trauma to the tissue.

In another embodiment of the invention, a plurality of tissue dilators may be used in association with the retractor instrument 20 to sequentially dilate or retract tissue prior to insertion of the retractor members 22, 24 into the tissue opening. The tissue dilators may be provided via a dilation instrument set including guide rods or pins and/or one or more tissue dilators of varying size. In one embodiment, the dilation instrument set may include a number of dilator tubes in addition to the dilator tube 160 illustrated and described above. Specifically, the dilation instrument set may include a plurality of tissue dilator tubes having inner and outer tube diameters that sequentially increase in size. In one embodiment of the invention, a guide pin or rod may be initially inserted through the skin of the patient and into tissue to form a tissue opening. A first dilator tube may then be slid over the guide pin or rod until a distal end portion of the first dilator tube is positioned in the tissue opening to dilate or retract the tissue opening. A second dilator tube (such as the dilator tube 160) having an inner tube diameter greater than the outer tube diameter of the first dilator tube may then be axially displaced over the first dilator tube until a distal end portion of the second dilator tube is positioned in the tissue opening to further dilate or retract the tissue opening. Although the above described dilation method includes the use of two dilator tubes, it should be understood that any number of dilator tubes may be used, including a single dilator tube of three or more dilator tubes. It should also be understood that the retractor instrument 20 need not necessarily be used in conjunction with dilator tubes or other types of dilation instruments, but may instead be used alone to provide a working channel or space W in communication with the surgical site.

Once the distal end portion of the last dilator tube is positioned within the tissue opening, the retractor members 22, 24 may then be inserted over and axially displaced along the last dilator tube until the distal ends 40a of the retractor blade sidewalls 40 are inserted into the tissue opening to provide additional dilation or retraction of the tissue. The dilator instruments may then be removed from the patient, thereby providing a working channel or space W from an area outside of the patient to the surgical site. The actuator device 28 may then be used to increase the size of the working channel or space via separation of the retractor members 22, 24 generally along the transverse axis T via linear and/or pivotal displacement of the retractor members 22, 24 relative to one another. The pin members 26a, 26b are then inserted through the axial passages 50 in the retractor blade sidewalls 40 until the distal end portions 70 of the pin members 26a, 26b are engaged with bone tissue, thereby securely engaging and anchoring the retractor members 22, 24 to bone to prevent the retractor instrument 20, and more particularly the retractor blades 30, from moving during the surgical procedure. In another embodiment, the pin members 26a, 26b may be inserted through the axial passages 50 in the retractor blade sidewalls 40 prior to separation of the retractor members 22, 24. In this manner, if the pin members 26a, 26b are engaged with separate bone segments (such as adjacent vertebral bodies), separation of the retractor members 22, 24 may be used to distract the bone segments away from one another.

As indicated above, the lateral opening 52 in the sidewall 40 which communicates with the axial passage 50 is sized and configured such that at least a portion of the pin member 26a, 26b is visible therethrough. As shown in FIG. 4, the distal end portion 70 of the pin member 26a is visible through the lateral opening 50 adjacent the distal end 40a of the retractor sidewall 40 as the pin member 26a is inserted through the axial passage 50 for engagement with bone tissue. More specifically, the pointed or tapered distal end 72 of the pin member 26a is visible through the enlarged portion 58 of the lateral opening 50 adjacent the distal end 40a of the retractor sidewall 40 as the pin member 26a is inserted through the axial passage 50. In this manner, the distal end 72 of the pin member 26a may be visualized by the surgeon during insertion of the pin member 26a through the axial passage 50 to ensure that the distal end 72 of the pin member 26a does not puncture or damage anatomic structures adjacent the distal end 40a of the retractor sidewall 40. Such anatomic structures may include, for example, soft tissue, neural structures, vascular structures, or any other anatomic structure subject to damage by the pin member 26a extending from the distal end 40a of the retractor sidewall 40. Visualization of the pin member 26a through the lateral opening 52 may occur via direct visualization by the surgeon or via viewing instruments including, for example, endoscopic or microscopic viewing elements or fluoroscopic instruments. Such viewing instruments can also be used to facilitate visualization of the working channel W and the surgical site.

Additionally, other instrumentation may be used in association with the retractor instrument 20, including nerve root retractors, tissue retractors, forceps, cutters, drills, scrapers, reamers, separators, rongeurs, taps, cauterization instruments, irrigation/aspiration instruments, illumination instruments, and/or inserter instruments, for use in performing surgical procedures through the working channel W. Additionally, bone, tissue, disc material, or other matter can be removed from the surgical site via the working channel W, and/or implants, such as fusion devices, screws, plates, rods, artificial discs, bone growth material, and other repair devices or therapeutic substances, can be inserted through the working channel W to the surgical site. Furthermore, the openings in the vertebrae within which the pin members 26a, 26b are initially positioned may be used as anchor or fixation points for subsequent attachment of one or more implants to the spinal column. Such implants may include, for example, rods, plates, wires, tethers or other types of elongate support elements or implant devices, including interbody implants. Additionally, such implants may be attached to the spinal column via a number of bone anchors including, for example, bone screws, pins, nails, bolts, staples or other types of bone anchor devices that would occur to one of skill in the art. Alternatively, the pin members 26a, 26b which initially anchor the retractor instrument 20 to the adjacent vertebral bodies may be used to attach one or more implants to the spinal column.

Figure 8:
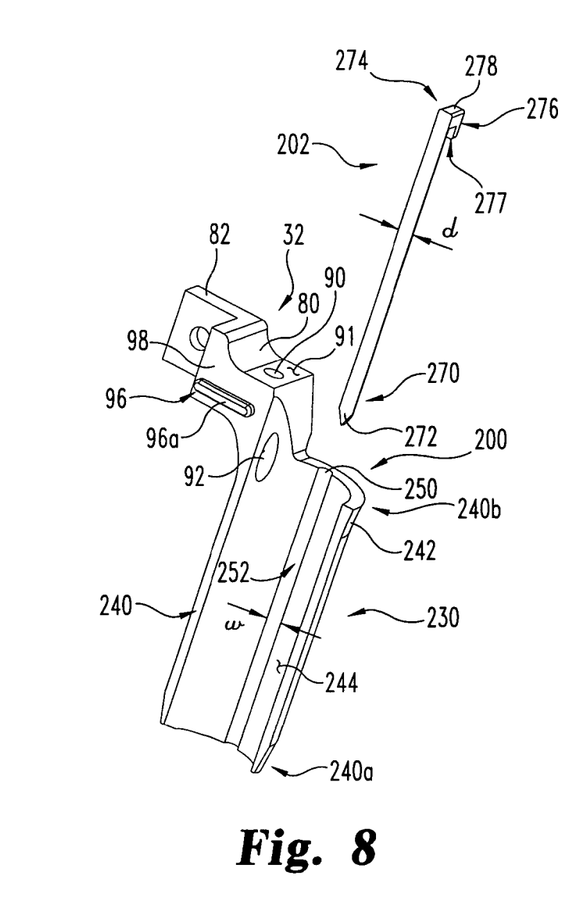
FIG. 8 is a perspective view of a retractor blade and pin member according to another embodiment of the present invention, as shown in a non-assembled state.
Figure 9:
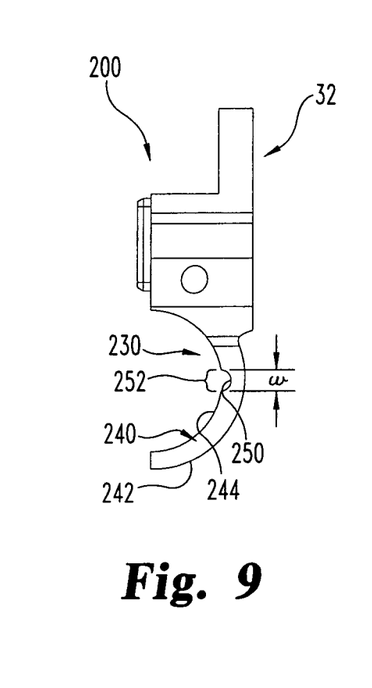
FIG. 9 is a top view of the retractor blade illustrated in FIG. 8.
Figure 10:
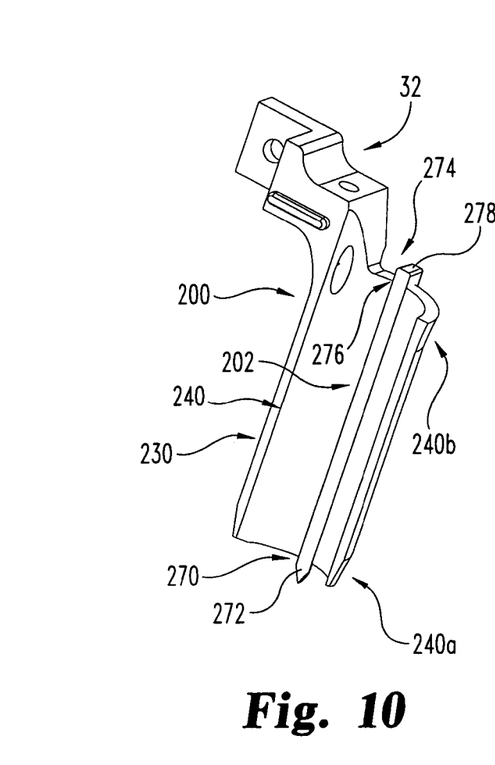
FIG. 10 is a perspective view of the retractor blade and pin member illustrated in FIG. 8, as shown in an assembled state.

Referring to FIGS. 8-10, illustrated therein is a retractor member 200 and pin member 202 according to other embodiments of the present invention for use in association with the retractor instrument 20. Similar to the retractor members 22, 24 illustrated and described above, the retractor member 200 includes a blade portion 230 for retracting tissue and a coupler portion 32 for mounting the blade portion 230 to the actuator device 28. In the illustrated embodiment, the coupler portion 32 is configured identical to the coupler portion 32 illustrated and described above with regard to the retractor members 22, 24. However, other types and configurations of the coupler portion 32 are also contemplated.

In the illustrated embodiment, the retractor blade 230 is configured similar to the retractor blade 30 illustrated and described above, including a sidewall 240 having a length extending between a distal end 240a and a proximal end 240b, and including an exterior surface 242 and an interior surface 244. The sidewall 240 also defines an axial passage 250 which extends along the sidewall length between the distal and proximal ends 240a and 240b and which is sized and configured to receive the pin member 202 therein. The sidewall 240 further defines a lateral opening 252 extending through the inner surface 244 of the sidewall 240 in transverse communication with the axial passage 250. However, unlike the lateral opening 52 of the retractor blade 30 which has a width w sized less than the outer diameter d of the pin member, the lateral opening 252 of the retractor blade 230 has a width w extending across the full width of the axial passage 250 and approximately equal to the outer dimension d of the pin member 202. As a result, the entire width w of the pin member 202 is visible when positioned within the axial passage 250 (FIG. 10).

In the illustrated embodiment, the axial passage 250 and the lateral opening 252 extend along the entire length of the sidewall 240. However, in other embodiments, the axial passage 250 and/or the lateral opening 252 may extend along less than the entire length of the sidewall 240. Additionally, although the lateral opening 252 is illustrated as extending through the interior surface 244 of the sidewall 240, in other embodiments, the lateral opening 252 may be arranged to extend through the exterior surface 242 of the sidewall 240. Further, although the axial passage 250 is illustrated as having a semi-circular inner cross section, it should be understood that other shapes and configurations of the axial passage 250 are also contemplated.

Similar to the pin members 26a, 26b illustrated and described above, the pin member 202 is configured to couple the retractor member 200 to one or more anatomic structures adjacent the surgical site, such as, for example, to one or more vertebral bodies. As shown in FIG. 10, the pin member 202 is positioned within the axial passage 250 of the retractor blade 230 and is sized such that a distal portion 270 of the pin member 202 extends beyond the distal end 240a of the retractor sidewall 240 for engagement with vertebral bone. In the illustrated embodiment, the distal portion 270 of the pin member 202 defines a pointed or tapered end 272 to facilitate penetration into bone tissue. However, unlike the pin members 26a, 26b, the pin member 202 does not include external threads for threading engagement with bone tissue. Instead, the pin member 202 is configured more like a nail which is impacted into bone tissue via application of an impaction force onto a proximal portion 274 of the pin member 202.

In the illustrated embodiment, the proximal portion 274 of the pin member 202 includes a hooked portion 276 defining a U-shaped recess 277 sized to receive the proximal end 240b of the retractor sidewall 240 therein to retain the pin member 202 within the axial passage 250. The proximal portion 274 of the pin member 202 is also provided with a relatively flat impaction surface 278 to facilitate driving engagement of the pin member 202 into bone tissue. Engagement of the hooked portion 276 of the pin member 202 with the proximal end 240b of the sidewall 240 compress the distal end 240a of the sidewall 240 into abutting engagement with the bone tissue. In the illustrated embodiment, the pin member 202 has a generally semi-circular outer cross section which corresponds to the inner cross section of the axial passage 250 extending through the retractor blade 230. However, it should be understood that other shapes and configurations of the pin member 202 are also contemplated.

Figure 11:
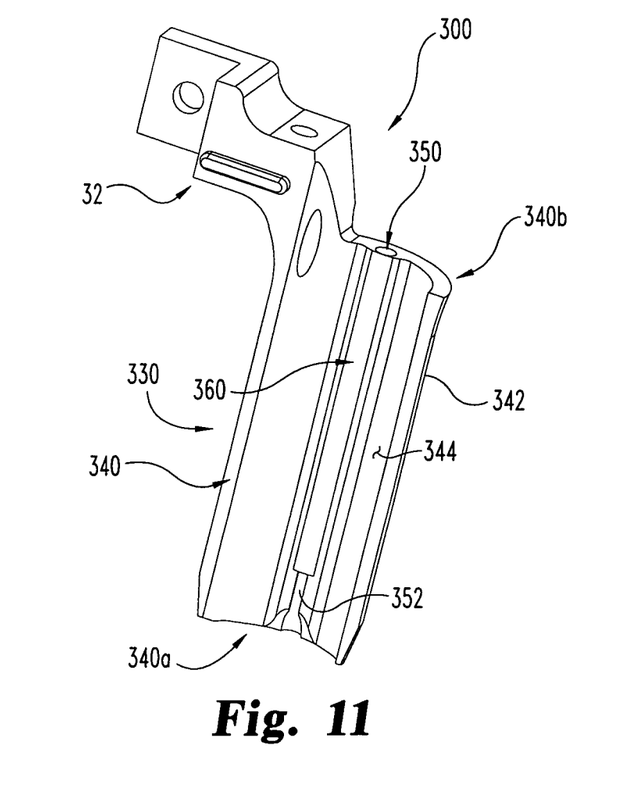
FIG. 11 is a perspective view of a retractor blade according to another embodiment of the present invention.

Referring to FIG. 11, illustrated therein is a retractor member 300 according to another embodiment of the present invention for use in association with the retractor instrument 20. Similar to the retractor members 22, 24 illustrated and described above, the retractor member 300 includes a blade portion 330 for retracting tissue and a coupler portion 32 for mounting the blade portion 330 to the actuator device 28. In the illustrated embodiment, the coupler portion 32 is configured identical to the coupler portion 32 illustrated and described above with regard to the retractor members 22, 24. However, other types and configurations of the coupler portion 32 are also contemplated.

In the illustrated embodiment, the retractor blade 330 is configured similar to the retractor blade 30 illustrated and described above, including a sidewall 340 having a length extending between a distal end 340a and a proximal end 340b, and including an exterior surface 342 and an interior surface 344. The sidewall 340 also defines an enlarged sidewall portion 360 extending along the sidewall length, and an axial passage 350 which extends through the enlarged sidewall portion 360 between the distal and proximal ends 340a and 340b and which is sized and configured to receive one of the pin members 26a, 26b therein. The sidewall 340 further defines a lateral opening 352 extending through the inner surface 344 of the sidewall 340 in transverse communication with the axial passage 350. However, unlike the lateral opening 52 of the retractor blade 30 which extends along the entire length of the retractor sidewall 40, the lateral opening 352 of the retractor blade 330 only extends along the distal portion of the retractor sidewall 340 adjacent the distal end 340a. As a result, only the distal portion of the pin member 26a, 26b is visible through the lateral opening 352 when positioned within the axial passage 350. In the illustrated embodiment, the lateral opening 352 is illustrated as extending through the interior surface 344 of the sidewall 340. However, in other embodiments, the lateral opening 352 may extend through the exterior surface 342 of the sidewall 340.

Figure 12:
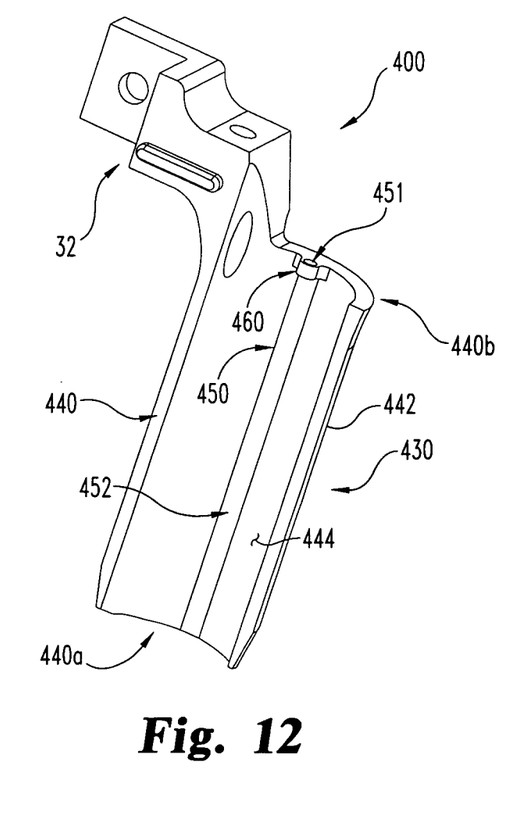
FIG. 12 is a perspective view of a retractor blade according to another embodiment of the present invention.
Figure 13:
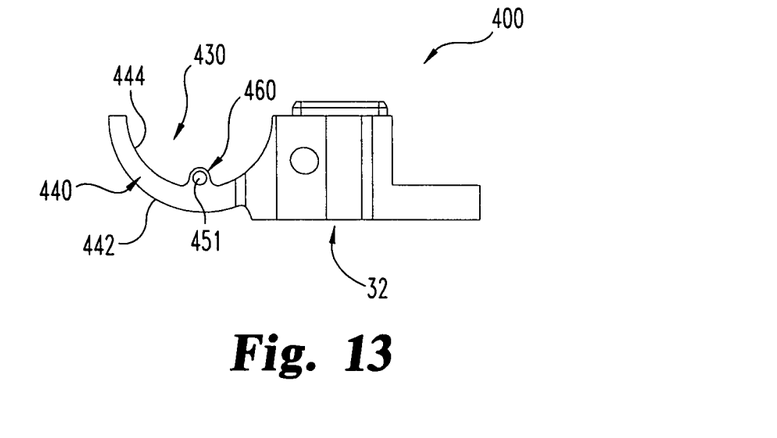
FIG. 13 is a top view of the retractor blade illustrated in FIG. 12.

Referring to FIGS. 12 and 13, illustrated therein is a retractor member 400 according to another embodiment of the present invention for use in association with the retractor instrument 20. Similar to the retractor members 22, 24 illustrated and described above, the retractor member 400 includes a blade portion 430 for retracting tissue and a coupler portion 32 for mounting the blade portion 430 to the actuator device 28. In the illustrated embodiment, the coupler portion 32 is configured identical to the coupler portion 32 illustrated and described above with regard to the retractor members 22, 24. However, other types and configurations of the coupler portion 32 are also contemplated.

In the illustrated embodiment, the retractor blade 430 is configured similar to the retractor blade 30 illustrated and described above, including a sidewall 440 having a length extending between a distal end 440a and a proximal end 440b, and including an exterior surface 442 and an interior surface 444. The sidewall 440 defines an axial passage 450 which extends along the sidewall length between the distal and proximal ends 440a, 440b and which is sized and configured to receive one of the pin members 26a, 26b or the pin member 202 therein. The sidewall 440 further defines a lateral opening 452 extending through the inner surface 444 of the sidewall 440 in transverse communication with the axial passage 450. In the illustrated embodiment, the axial passage 450 and the lateral opening 452 extend along substantially the entire length of the sidewall 440. However, in other embodiments, the axial passage 450 and/or the lateral opening 452 may extend along less than the entire length of the sidewall 440. Additionally, although the lateral opening 452 is illustrated as extending through the interior surface 444 of the sidewall 440, in other embodiments, the lateral opening 452 may be arranged to extend through the exterior surface 442 of the sidewall 440. Further, although the axial passage 450 is illustrated as having a semi-circular inner cross section, it should be understood that other shapes and configurations of the axial passage 450 are also contemplated.

The sidewall 440 also defines an enlarged sidewall portion 460 extending laterally from interior surface 444 adjacent the proximal end 440b. The enlarged sidewall portion 460 includes an aperture 451 in generally alignment and axial communication with the axial passage 450. The aperture 451 is sized to receive a portion of the pin member therein to retain the pin member in position relative to the retractor blade 430. The aperture 451 may also function to guide the pin member along the retractor sidewall 440 as the pin member is engaged with the retractor blade 430. In the illustrated embodiment of the invention, the enlarged sidewall portion 460 is positioned adjacent the proximal end 440b of the retractor sidewall 440. However, it should be understood that the enlarged sidewall portion 440 may be positioned along other portions of the retractor sidewall 440. Additionally, although the retractor blade 430 is illustrated as including a single enlarged sidewall portion 460, it should be understood that the retractor blade 430 may include multiple enlarged sidewall portions 460 located intermittently along the length of the retractor blade 430. It should further be understood that the retractor blade 430 need not necessarily include a separate axial passage 450. Instead, the pin member may be retained in position relative to the retractor blade 430 via insertion through the apertures 451 in one or more of the enlarged sidewall portions 460. Furthermore, although the enlarged sidewall portion 460 is illustrated as extending from the interior surface 444 of the retractor sidewall 440, it should be understood that the enlarged sidewall portion 460 may be configured to extend from the exterior surface 442 of the retractor sidewall 440

Figure 14:
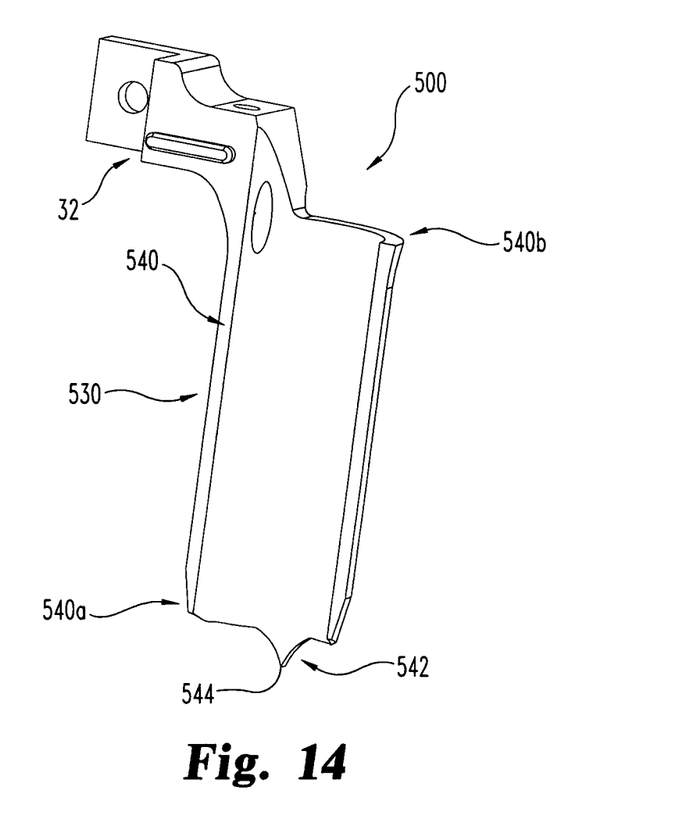
FIG. 14 is a perspective view of a retractor blade according to another embodiment of the present invention.

Referring to FIG. 14, illustrated therein is a retractor member 500 according to another embodiment of the present invention for use in association with the retractor instrument 20. Similar to the retractor members 22, 24 illustrated and described above, the retractor member 500 includes a blade portion 530 for retracting tissue and a coupler portion 32 for mounting the blade portion 530 to the actuator device 28. In the illustrated embodiment, the coupler portion 32 is configured identical to the coupler portion 32 illustrated and described above with regard to the retractor members 22, 24. However, other types and configurations of the coupler portion 32 are also contemplated. In the illustrated embodiment, the retractor blade 530 is configured similar to the retractor blade 30 illustrated and described above, including a sidewall 540 having a length extending between a distal end 540a and a proximal end 540b.

However, unlike the retractor blade 30, the retractor blade 530 does not include an axial passage for receipt of a pin member therethrough, nor does the retractor blade 530 include a lateral opening for visualization of a pin member. Instead of using a separate pin member to anchor the retractor blade 530 to bone tissue, the retractor blade 530 is provided with an integral anchor member 542 extending from the distal end 540a of the retractor sidewall 540. In the illustrated embodiment, the anchor member 542 is configured as a triangular-shaped tooth or projection having a pointed or tapered distal end 544 to facilitate penetration into bone tissue. However, it should be understood that other types and configurations of anchor members are also contemplated for anchoring the retractor blade 530 to bone tissue. Additionally, although the retractor blade 530 is illustrated as including a single anchor member 542, it should be understood that the retractor blade 530 may be provided with a plurality of anchor members 542. Furthermore, although the anchor member 542 is illustrated as being formed integral with the retractor blade 530 in a static or stationary position, it should be understood that the anchor member 542 may be formed separately from and coupled to the retractor blade 530, and may be configured to deploy subsequent to positioning of the retractor blade 530 adjacent the surgical site.

While the invention has been illustrated and described in detail in the drawings and foregoing description, the same is to be considered as illustrative and not restrictive in character, and that all changes and modifications that come within the spirit of the invention are desired to be protected.

What is claimed is:

1. Instrumentation for retracting tissue, comprising:
a retractor member including a sidewall extending along a longitudinal axis, said sidewall having a length extending between a distal end and a proximal end, the proximal end connected with a coupling portion comprising a first end extending entirely between and connecting opposite first and second sides of said coupling portion, said coupling portion comprising a second end opposite said first end, said second end extending entirely between and connecting said first and second sides, said first and second sides extending perpendicular to said longitudinal axis, said sidewall being connected to said first end such that one of said first and second sides and an inner surface of said sidewall face a common direction and the length of the sidewall is invariable, said sidewall defining an axial passage extending into a thickness of said sidewall continuously along said length, said sidewall defining a lateral opening extending through said inner surface that is in transverse communication with said axial passage, said lateral opening extending continuously along said length, the lateral opening being sized larger adjacent the distal end of the sidewall relative to other portions of the lateral opening, said coupling portion including a first opening, said sidewall including a second opening, said first and second openings being spaced apart from said axial passage and said lateral opening, said first and second openings being connected by an enclosed passageway such that instrumentation can be passed into the first opening, through the passageway and out the second opening into a working channel defined by the retractor member; and a pin member disposed within said axial passage and including a distal end portion positionable adjacent said distal end of said retractor member with at least a portion of said pin member positioned adjacent and visible through said lateral opening adjacent said distal-most end of said sidewall.

2. The instrumentation of claim 1, wherein said axial passage and said lateral opening each extend entirely along said length from said distal end to said proximal end of said retractor member.

3. The instrumentation of claim 1, wherein said sidewall of said retractor member includes an enlarged axial region extending generally along said length, said axial passage extending through said enlarged axial region.

4. The instrumentation of claim 3, wherein said enlarged axial region and said axial passage each extend entirely along said length of said retractor member from said distal end to said proximal end.

5. The instrumentation of claim 3, wherein said enlarged axial region defines a lateral protrusion extending transversely from a lateral surface of said sidewall, said lateral protrusion defining said lateral opening.

6. The instrumentation of claim 3, further comprising a tissue dilator tube including a tube wall having a tube length, said tube wall defining at least one groove extending axially along said tube length and sized to slidably receive said enlarged axial region of said retractor member therein as said retractor member is axially displaced relative to said dilator tube.

7. The instrumentation of claim 1, wherein said retractor member has a tubular configuration defining said working channel extending generally along said longitudinal axis and entirely along said length.

8. The instrumentation of claim 7, wherein said lateral opening is positioned in communication with said working channel.

9. The instrumentation of claim 1, wherein said pin member is sized and configured such that said distal end portion extends from said distal end of said retractor member and into engagement with bone tissue.

10. The instrumentation of claim 9, wherein said distal end portion of said pin member is threaded for threading engagement with the bone tissue.

11. The instrumentation of claim 9, wherein said pin member is non-threaded.

12. The instrumentation of claim 1, wherein the lateral opening comprises a width that is less than a diameter of the pin member.

13. The instrumentation of claim 1, wherein said working channel extends generally along said longitudinal axis and entirely along said length, said first opening extends through a face of said coupling portion that extends between said first and second sides of said coupling portion, and said second opening extends through said inner surface.

14. The instrumentation of claim 1, wherein said sidewall is monolithically formed with said coupling portion.

15. Instrumentation for retracting tissue, comprising:

a retractor assembly including at least two retractor members that cooperate to define a working space therebetween extending generally along a longitudinal axis, each of said at least two retractor members including a sidewall having a length extending between a distal end and a proximal end, the proximal end connected with a coupling portion extending perpendicular to said longitudinal axis such that the distal end is fixed along the longitudinal axis relative to the coupling portion and the length of the sidewall is invariable, at least one of said sidewalls defining an axial passage extending into a thickness of said sidewall continuously along said length and defining a lateral opening in transverse communication with said axial passage, said lateral opening extending continuously along said length, the lateral opening being sized larger adjacent the distal end of the sidewall relative to other portions of the lateral opening, said coupling portion including a first opening, said sidewall including a second opening, said first and second openings being spaced apart from said axial passage and said lateral opening, said first and second openings being connected by an enclosed passageway such that a surgical instrument can be passed into the first opening, through the passageway and out the second opening into a working channel defined by the retractor member; and a pin member disposed within said axial passage and including a distal end portion positionable adjacent said distal end of said retractor member with at least a portion of said pin member positioned adjacent and visible through said lateral opening adjacent said distal-most end of said sidewall, wherein said coupling portion comprises a first end extending entirely between and connecting opposite first and second sides of said coupling portion, said coupling portion comprising a second end opposite said first end, said second end extending entirely between and connecting said first and second sides, said first and second sides extending perpendicular to said longitudinal axis, said sidewall being connected to said first end such that one of said first and second sides and an inner surface of said sidewall face a common direction, wherein the coupling portion of one of said retractor members comprises an aperture extending from a respective second side and the coupling portion of another of said retractor members comprises a protrusion extending into a respective second side such that said protrusion faces said aperture, said protrusion being configured for disposal in said aperture to align respective retractor members.

16. The instrumentation of claim 15, wherein said axial passage and said lateral opening each extend entirely along said length of said retractor member from said distal end to said proximal end.

17. The instrumentation of claim 15, wherein said lateral opening is positioned in communication with said working space.

18. The instrumentation of claim 15, wherein a first of said at least two retractor members includes a first pair of longitudinal edges extending along said length between said distal and proximal ends;

wherein a second of said at least two retractor members includes a second pair of longitudinal edges extending along said length between said distal and proximal ends; and wherein said first pair of longitudinal edges is positioned adjacent said second pair of longitudinal edges to provide a retractor assembly having a tubular configuration substantially enclosing said working space.

19. The instrumentation of claim 15, wherein:
each of said sidewalls includes a sidewall protrusion projecting transversely from an inner surface thereof and extending axially along at least a portion of said length; and
said instrumentation further comprises a tissue dilator tube including a tube wall having a tube length, said tube wall defining at least two recesses each extending axially along said tube length and sized to slidably receive a respective one of said sidewall protrusions therein as said retractor member is axially displaced relative to said dilator tube.

20. The instrumentation of claim 19, wherein said at least one recess extends along an exterior surface of said tube wall and entirely along said tube length; and
wherein said retractor member has a tubular configuration having an inner diameter greater than an outer diameter of said dilator tube such that said retractor member is axially displaceable over said dilator tube with said sidewall protrusion slidably displaced along said recess.

21. The instrumentation of claim 15, wherein said pin member is non-threaded.

22. The instrumentation of claim 15, wherein said surgical instrument is a light source or viewing source.

23. Instrumentation for retracting tissue, comprising:
a retractor member including a sidewall extending along a longitudinal axis and having a length extending between a distal end and a proximal end, the proximal end connected with a coupling portion comprising a first end extending entirely between and connecting opposite first and second sides of said coupling portion, said coupling portion comprising a second end opposite said first end, said second end extending entirely between and connecting said first and second sides, said first and second sides extending perpendicular to said longitudinal axis, said sidewall being connected to said first end such that one of said first and second sides and an inner surface of said sidewall face a common direction and the length of the sidewall is invariable, said sidewall including a main sidewall portion defining a first wall thickness, said sidewall including an enlarged sidewall portion extending axially along at least a portion of said length and defining a second wall thickness greater than said first wall thickness, said sidewall defining an axial passage extending continuously along said length through said enlarged sidewall portion and said inner surface without extending through an outer surface of said sidewall, said coupling portion including a first opening, said sidewall including a second opening, said first and second openings being spaced apart from said axial passage, said first and second openings being connected by an enclosed passageway such that instrumentation can be passed into the first opening, through the passageway and out the second opening into a working channel defined by the retractor member;
a pin member disposed within said axial passage and including a distal end portion positionable adjacent said distal end of said retractor member; and
a tissue dilator tube including a tube wall having a tube length, said tube wall defining at least one groove extending axially along said tube length and sized to slidably receive said enlarged sidewall portion of said retractor member therein as said retractor member is axially displaced relative to said dilator tube,
wherein said enlarged sidewall portion and said axial passage each extend entirely along said length from said distal end to said proximal end of said retractor member.

24. The instrumentation of claim 23, wherein a section of said sidewall axial passage that extends through said inner surface defines a lateral opening in transverse communication with said axial passage, at least a portion of said pin member being visible through said lateral opening.

25. The instrumentation of claim 24, wherein said enlarged sidewall portion of said retractor member defines a lateral protrusion extending transversely from a lateral surface of said main sidewall portion, said lateral protrusion defining said lateral opening.

26. The instrumentation of claim 23, wherein said retractor member has a tubular configuration, said inner surface defining said working channel, said working channel extending generally along said longitudinal axis and entirely along said length; and
wherein said lateral opening is positioned in communication with said working channel.

27. The instrumentation of claim 23, wherein said at least one groove of said dilator tube extends entirely along said tube length.

28. The instrumentation of claim 23, wherein said at least one groove of said dilator tube extends along an exterior surface of said tube wall.

29. The instrumentation of claim 23, wherein said enlarged sidewall portion of said retractor member and said at least one groove of said dilator tube each have an arcuate profile.

30. The instrumentation of claim 23, wherein said retractor member has a tubular configuration defining an inner diameter greater than an outer diameter of said dilator tube such that said retractor member is axially displaceable over said dilator tube with said enlarged sidewall portion slidably displaced along said at least one groove.

31. The instrumentation of claim 23, further comprising a plurality of tissue dilator tubes, a first of said dilator tubes having an outer tube diameter and including a distal end portion positionable in a tissue opening, a second of said dilator tubes having an inner tube diameter greater than said outer tube diameter such that said second dilator tube is axially displaceable over said first dilator tube with a distal end portion of said second dilator tube positionable within the tissue opening to further dilate the tissue opening; and
wherein said retractor member has a tubular configuration having an inner diameter greater than said outer diameter of said second dilator tube such that said retractor member is axially displaceable over said second dilator tube with a distal end portion of said retractor member positionable within the tissue opening.

32. The instrumentation of claim 31, wherein said second dilator tube includes a tube wall having a tube length, said tube wall defining a groove extending axially along said length and sized to slidably receive said enlarged sidewall portion of said retractor member therein as said retractor member is axially displaced over said second dilator tube.

33. The instrumentation of claim 23, wherein said sidewall defines a lateral opening in transverse communication with said axial passage, said lateral opening extending continuously along said length from a distal-most end of said sidewall to a location adjacent said proximal end; and
wherein said distal end portion of said pin member is positionable adjacent and visible through said lateral opening adjacent said distal end of said sidewall.

34. Instrumentation for retracting tissue, comprising:
a retractor member including a sidewall extending along a longitudinal axis, said sidewall having a length extending between a distal end and a proximal end, the proximal end connected with a coupling portion comprising a first end extending entirely between and connecting opposite first and second sides of said coupling portion, said coupling portion comprising a second end opposite said first end, said second end extending entirely between and connecting said first and second sides, said first and second sides extending perpendicular to said longitudinal axis, said sidewall being connected to said first end such that one of said first and second sides and a laterally-facing surface of said sidewall face a common direction and the length of the sidewall is invariable, said sidewall including a sidewall protrusion projecting transversely from said laterally-facing surface and extending axially along at least a portion of said length, said retractor member defining an axial passage extending continuously along said length such that a portion of said axial passage extends through said sidewall protrusion, said coupling portion including a first opening, said sidewall including a second opening, said first and second openings being spaced apart from said axial passage, said first and second openings being connected by an enclosed passageway such that instrumentation can be passed into the first opening, through the passageway and out the second opening into a working channel defined by the retractor member;
a pin member disposed within said axial passage and including a distal end portion positionable adjacent said distal end of said retractor member; and
a tissue dilator tube including a tube wall having a tube length, said tube wall defining at least one recess extending axially along said tube length and sized to slidably receive said sidewall protrusion of said retractor member therein as said retractor member is axially displaced relative to said dilator tube,
wherein said sidewall protrusion defines a lateral opening in transverse communication with said axial passage, said lateral opening extending continuously along said length from a distal-most end of said sidewall to a location adjacent said proximal end, and with at least a portion of said pin member positioned adjacent and visible through said lateral opening adjacent said distal-most end of said sidewall.

35. The instrumentation of claim 34, wherein said sidewall comprises a main sidewall portion including said laterally-facing surface and defining a first wall thickness, said sidewall protrusion defining a second wall thickness greater than said first wall thickness.

36. The instrumentation of claim 34, wherein said retractor member has a tubular configuration defining said working channel extending generally along said longitudinal axis and entirely along said length; and
wherein said sidewall protrusion projects inwardly into said working channel.

37. The instrumentation of claim 34, wherein the lateral opening is sized larger adjacent the distal end of the sidewall relative to other portions of the lateral opening.

38. The instrumentation of claim 34, wherein said sidewall protrusion and said axial passage each extend entirely along said length from said distal end to said proximal end.

* * * * *